United States Patent
Phillips, Jr.

(10) Patent No.: US 11,155,986 B2
(45) Date of Patent: Oct. 26, 2021

(54) TOILET ODOR ELIMINATION DEVICE

(71) Applicant: Aliese Phillips, Auburn, IL (US)

(72) Inventor: William Robert Phillips, Jr., Auburn, IL (US)

( * ) Notice: Subject to any disclaimer, the term of this patent is extended or adjusted under 35 U.S.C. 154(b) by 0 days.

(21) Appl. No.: 16/914,282

(22) Filed: Jun. 27, 2020

(65) Prior Publication Data

US 2020/0325670 A1  Oct. 15, 2020

Related U.S. Application Data

(63) Continuation-in-part of application No. 16/350,159, filed on Oct. 9, 2018, now abandoned.

(60) Provisional application No. 62/606,986, filed on Oct. 16, 2017.

(51) Int. Cl.
*E03D 9/052* (2006.01)
*B01D 46/00* (2006.01)
*B01D 46/24* (2006.01)
*B01D 39/20* (2006.01)
*A61L 9/014* (2006.01)
*E03D 9/00* (2006.01)

(52) U.S. Cl.
CPC .............. *E03D 9/052* (2013.01); *A61L 9/014* (2013.01); *B01D 39/2055* (2013.01); *B01D 46/0038* (2013.01); *B01D 46/0043* (2013.01); *B01D 46/24* (2013.01); *E03D 9/007* (2013.01); *A61L 2209/14* (2013.01); *A61L 2209/15* (2013.01); *A61L 2209/22* (2013.01); *B01D 2271/02* (2013.01)

(58) Field of Classification Search
CPC ...................................................... E03D 9/052

USPC ........................................................ 4/213, 209
See application file for complete search history.

(56) References Cited

U.S. PATENT DOCUMENTS

| | | | | |
|---|---|---|---|---|
| 3,066,317 A | * | 12/1962 | Cawiezel | E03D 9/052 4/213 |
| 3,120,006 A | * | 2/1964 | Knappe | E03D 9/052 4/213 |
| 3,469,267 A | * | 9/1969 | Kuklok | E03D 9/05 4/213 |
| 4,318,192 A | * | 3/1982 | Williams | E03D 9/052 4/213 |
| 4,402,091 A | * | 9/1983 | Ellis | E03D 9/052 4/217 |
| 4,583,250 A | * | 4/1986 | Valarao | E03D 9/052 4/209 R |
| 5,010,600 A | * | 4/1991 | Prisco | E03D 9/052 4/211 |
| 5,029,346 A | * | 7/1991 | Fernald, Sr. | E03D 9/052 4/213 |
| 5,054,130 A | * | 10/1991 | Wilson | E03D 9/052 4/213 |
| 5,170,512 A | * | 12/1992 | Prisco | E03D 9/052 4/213 |

(Continued)

*Primary Examiner* — Lori L Baker
(74) *Attorney, Agent, or Firm* — Law Offices of Robert M. Patino

(57) ABSTRACT

A toilet odor elimination device that resides below a water tank lid of a water tank includes a housing with an intake chamber, a filter chamber in operational relationship to a micro fan chamber, a tubular exhaust tube and an at least one battery storage chamber. The toilet odor elimination device is activated by an on/off switch that resides in an electrical relationship to a power source located in the at least one battery storage chamber.

12 Claims, 9 Drawing Sheets

(56) References Cited

U.S. PATENT DOCUMENTS

| | | | | |
|---|---|---|---|---|
| 5,355,536 A * | 10/1994 | Prisco | E03D 9/052 | 4/217 |
| 5,435,018 A * | 7/1995 | Nishimoto | E03D 9/007 | 4/213 |
| 5,519,899 A * | 5/1996 | Taylor | E03D 9/04 | 4/349 |
| 5,539,938 A * | 7/1996 | Tubbs | E03D 1/142 | 4/213 |
| 5,606,747 A * | 3/1997 | Dupont | E03D 9/05 | 4/213 |
| 5,652,969 A * | 8/1997 | Taylor | E03D 3/10 | 4/213 |
| 5,906,009 A * | 5/1999 | Sakar | E03D 9/05 | 4/216 |
| 6,279,173 B1 * | 8/2001 | Denzin | E03D 9/05 | 4/213 |
| 6,804,837 B1 * | 10/2004 | Guess, Sr. | E03D 9/052 | 4/213 |
| 6,948,192 B2 * | 9/2005 | Hipponsteel | E03D 9/05 | 4/213 |
| 7,103,925 B2 * | 9/2006 | Toth | A47K 13/307 | 4/213 |
| 7,849,523 B2 | 12/2010 | Crittenden et al. | | |
| 7,856,675 B1 * | 12/2010 | Couturier | E03D 9/052 | 4/213 |
| 8,060,952 B2 * | 11/2011 | Shaul | E03D 9/05 | 4/216 |
| 8,161,579 B2 * | 4/2012 | Denkewicz, Jr. | E03D 9/052 | 4/213 |
| 8,214,930 B2 * | 7/2012 | Azodi | E03D 9/05 | 4/213 |
| 8,337,602 B2 * | 12/2012 | Foerster | A61L 9/014 | 96/147 |
| 8,656,524 B2 * | 2/2014 | McKiernan | E03D 11/11 | 4/319 |
| 9,957,702 B1 * | 5/2018 | Da Silva | E03D 9/04 | |
| 10,744,736 B2 * | 8/2020 | Burwell | B32B 3/266 | |
| 2003/0019019 A1 * | 1/2003 | Blanch | E03D 9/05 | 4/213 |
| 2004/0083541 A1 * | 5/2004 | Ogren | E03D 9/052 | 4/213 |
| 2008/0307570 A1 * | 12/2008 | Marks | E03D 9/052 | 4/213 |
| 2009/0056007 A1 * | 3/2009 | Pham | E03D 9/052 | 4/347 |
| 2013/0263367 A1 * | 10/2013 | Ceja Estrada | E03D 9/05 | 4/213 |
| 2013/0276220 A1 * | 10/2013 | Cogswell | E03D 9/052 | 4/352 |
| 2014/0304903 A1 * | 10/2014 | Cogswell | A47K 17/00 | 4/314 |
| 2014/0338111 A1 * | 11/2014 | Zheng | E03D 9/052 | 4/213 |
| 2017/0183854 A1 * | 6/2017 | Hobson | B01D 46/0038 | |

\* cited by examiner

-Prior Art-

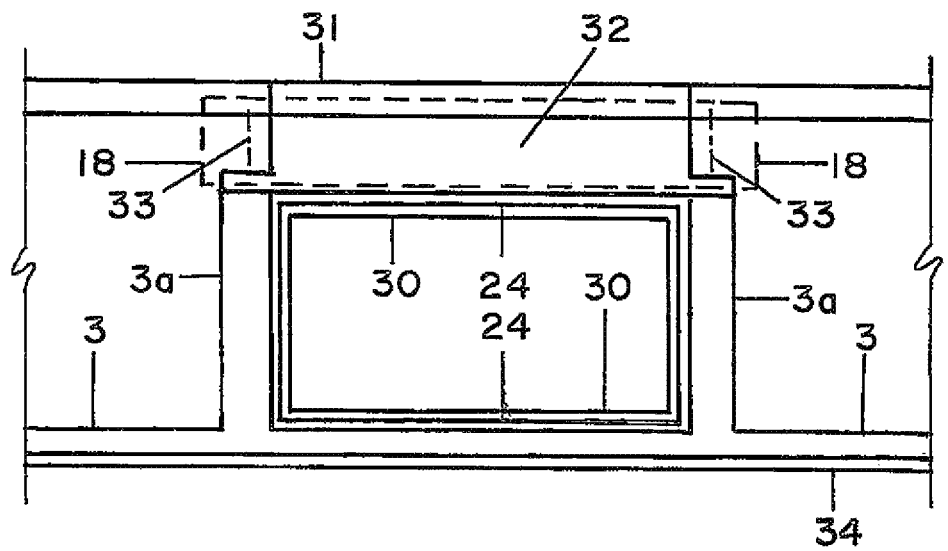
Fig. 13
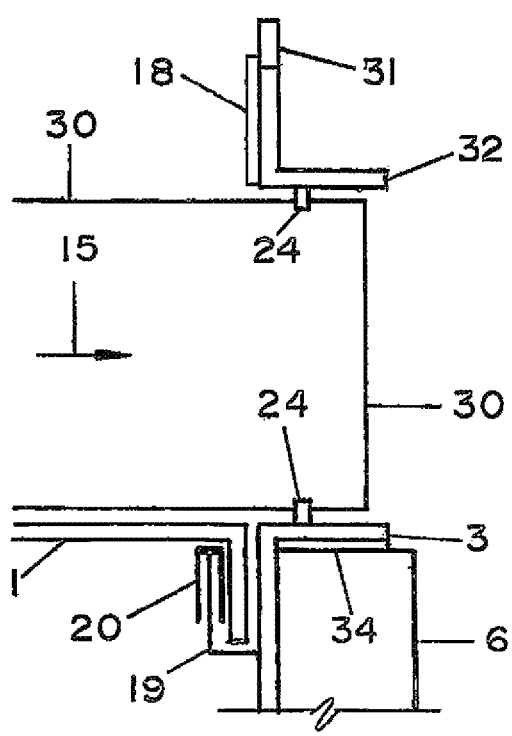 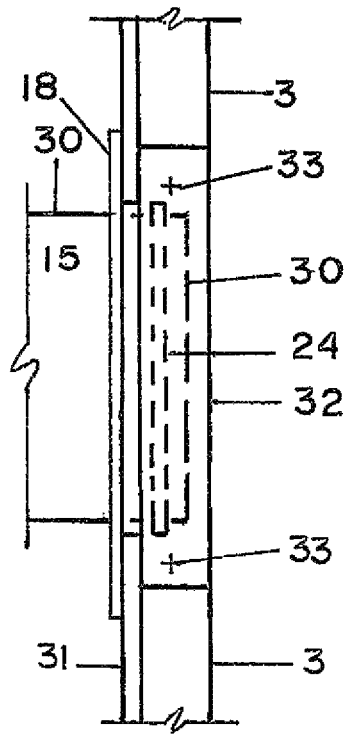
Fig. 14  Fig. 15

TOILET ODOR ELIMINATION DEVICE

CROSS REFERENCE TO RELATED APPLICATIONS

This application is a continuation-in-part of, and claims the benefit of priority to, U.S. utility patent application Ser. No. 16/350,159 filed on Oct. 9, 2018, which relates to and claims priority to U.S. provisional patent application Ser. No. 62/606,986 filed on Oct. 16, 2017. The disclosure of each of the above-reference patent applications is expressly incorporated by reference herein in its entirety.

BACKGROUND OF THE INVENTION

Flushing toilet bowls typically result in the release of malodorous odors beyond the toilet bowl in the adjacent air space. The traditional solution is the use of an actuated electrical fan to remove the malodorous odors. The fan is normally located in the same room as the toilet. The problem with this practice that is that the malodorous odors have already diffused into the room's air space, resulting in the saturation of the occupant's skin, clothes, and hair with these odors.

Previous inventions have attempted to address this issue in multiple manners. U.S. Pat. No. 5,606,747 by Dupont dated Mar. 4, 1997 discloses a device attached to the overflow tube containing a housing fan charcoal filter. This device has no apparent way of changing the filter. Furthermore, this invention has possible conflicts with the present water tank floats and other operational mechanisms. U.S. Pat. No. 5,054,130 by Wilson dated Oct. 8, 1991 discloses a deodorizer attached to the exterior of the water tank. U.S. Pat. No. 6,279,173 to Assignee D2M Inc. dated Aug. 28, 2001 discloses a fan attached to the interior of the water tank using air up flow through a tube. The air is then filtered and exhausted in the water tank. This device is apparently not used in conventional flush toilets using a float actuated system. Furthermore this design does not appear to have replaceable filters and with the size of the fan and operation motor, unwanted noised may be produced. U.S. Pat. No. 4,583,250 to Valarao dated Apr. 22, 1986 discloses a large filtering unit attached to the top of toilet with an air supply flow hook up on the fill tube that pulls air up through the device. Air is then forced out of device through the filter and exits into the room. This device is a large addition to a toilet in order solve the malodorous air problem. Furthermore, it is a possible electrical hazard due to its location. Moreover, this device cannot fit all toilets.

Other proposed solutions include U.S. Pat. No. 4,318,192 by Williams dated Mar. 9, 1982 which discloses a device which is placed in the water tank. This device will take up space reserved for water storage in the tank which can cause the toilet to have an inadequate volume of water to move the waste in the bowl through the waste line. Furthermore, this device also does not appear to be installable on conventional flush toilets using a float actuated system. This device appears to jeopardize the toilet's siphon abilities to remove the waste due to the device being tapped into the waste line. U.S. Pat. No. 7,849,523 to Smith which is dated Dec. 14, 2010 discloses a fan device mounted inside the water tank and a flush tube being capped to supply the device with malodorous air from the bowl. This device treats the malodorous odor the device discharges via a line directly tapped into toilets waste line which may cause a siphon problem. Furthermore, this device requires the manufacturer to place a discharge line in its production which is costly and cumbersome. U.S. Pat. No. 8,161,579 to Denkewicz dated Apr. 24, 2012 discloses devices which are attached internally within the water tank to a stand pipe with two (2) alternate designs. Both designs appear not to be used with a conventional float system. Furthermore, the devices take up storage area for the water which may impede the removal of waste in the bowl due to not meeting the minimal water volume requirement.

As such, there is a need for an air filtering device that can remove the malodorous odors that present themselves in toilet bowls that function with traditional float actuated systems. Furthermore, the device should be small enough and take up minimal space in the water reservoir so that an adequate volume of water is preserved to move the waste in the bowl through the waste line. The device should also be attached in a manner where it is simple to operate and manage the filtration needs of the device.

SUMMARY OF INVENTION

The present invention addresses these shortcomings of many of the prior art attempts to address the malodorous odors associated with the disposal of human waste in a toilet bowl. More particularly, the invention relates to an air filtering device which is attached to an existing toilet's water tank. The device is useful with tanks being interconnected with the toilet bowl and thereupon, is capable of filtering the malodorous odors without infringing or disrupting the water tank and bowl operation.

The invention is a device that can be installed in any conventional toilet regardless of the size or shape. This is a device that removes malodorous odors from the toilet bowl by pulling odors up through the holes in the bowl's rim with fans located in the device's housing. The housing is secured in the interior of the water tank above the waterline. After flowing from the holes, the malodorous odors are then dispensed up the fill tube, which is in direct communication with the holes. The malodorous odors exit the fill tube and is then confined in the water tank's presently sealed air space. The micro fans of the device then pulls the confined malodorous odor into the housing's intake chamber which is connected to the sealed filter tube. The malodorous odor then enters and flows through a filter tube which removes the malodorous odors creating cleaned air. The cleaned air then flows out of the filter tube and is then pulled into the airtight fan chamber by the fans. Then after flowing across the fans, the cleaned air is pushed by the fans into a sealed exhaust tube. The cleaned air is then pushed by the fans out of the exhaust tube and the clean air flows into the adjacent space. The device is preferably operated by a panel containing an on/off switch and a charging port which is secured to the exterior of the water tank for easy access.

Other features and details of this device will become clear and apparent upon examination of the following detailed description and drawings where like reference numbers to like parts are used throughout.

DESCRIPTION OF THE DRAWINGS

FIG. 13 is an exterior view, outside of the water tank, of a modified riser area that will seal the housing exhaust tube.

FIG. 14 is a cross-sectional view at the centerline of the modified riser area.

FIG. 15 is a plan view of the modified riser area as shown in FIG. 14.

DETAILED DESCRIPTION OF THE PREFERRED EMBODIMENTS

It is to be pointed out that the reference numbers used in this description are not restricted to an individual figure and may be used throughout the drawings and description. These reference numbers will always be used to denote the same component throughout.

Figure 1:
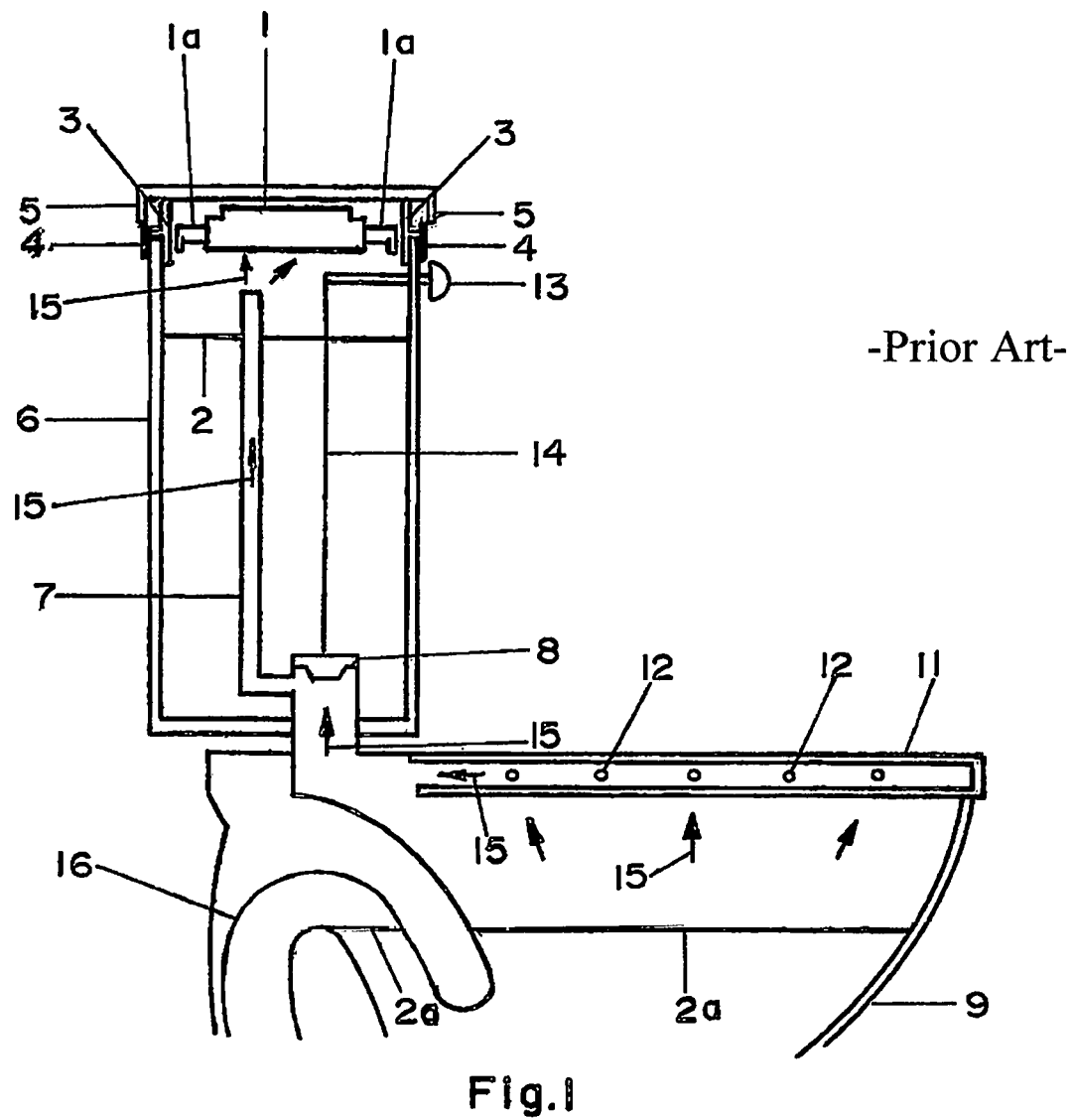
FIG. 1 is a cross-sectional view of a conventional toilet with the device installed along with directional arrows illustrating the resulting direction of air movement.

FIG. 1 is a cross sectional view of a conventional toilet with the invention called a device generically. The device and the convention toilet comprise of components such as a water tank lid 5, a water tank 6, a fill tube 7, a rubber flapper 8, a toilet bowl 9, bowl rim 11, a plurality of rim openings 12, an activating handle 13, a chain 14, a toilet waste line 16. The main components of this device include a housing 1, a support bracket arm 1, a riser 3, and an enclosure 4. This enclosure 4 is an option which is not detailed due to the different styles colors which are undeterminable at this time. The air flow 15 is shown as direction arrows and is generated from this device. Furthermore, an upper water level 2 is provided and a waste line water level 2*a* is also shown.

A conventional toilet operates with the water tank lid 5 in place. When finished having a bowel movement or other event that requires a flush, an operator pivots the activating handle 13.

This action in turn puts upward tension on the chain 14, resulting in the action of removing the rubber flapper 8 from a seeded position. The store water which resides at the upper water level 2 in the water tank 6 is allowed to flow into the toilet bowl 9 to remove the human waste or waste (collectively "the human waste") via the toilet waste line 16. This actuation also initiates the water supply to flow up the fill tube 7 and then water enters the toilet bowls rim 11, egressing through the plurality of rim openings 12 into the toilet bowl rim 11. The result is the of removal of the human waste and a rinsing toilet bowl 9. After the removal of the human waste, the rubber flapper 8 reseeds itself in the fill tube 7, which replenishes the water level in the toilet bowl 9 and its water tank 6 to its previous upper water level 2 and waste line water level 2*a*.

Several of the conventional toilet structural components that are drawn in FIG. 1 are for reference only. This device utilizes the airflow direction 15 that is generated by the conventional toilet. More particularly, after the previously explained flush operation is complete, the fill tube 7, which is in direct communication with the toilet bowl 9, is an open airway. This allows the device to pull the malodorous air out of the toilet bowl 9 upwards through the fill tube 7 into the confined air space that is located between the upper water level 2 in the water tank 6 and the water tank lid 5 upon activation of this device.

The housing 1 of the device is mounted within the perimeter of the water tank 6 and below the water tank lid 5 of the conventional flush toilet. The water tank 6 is accompanied with a flush operating system, which comprises of the activating handle 13 connected to the chain 14 connected to the flapper 8 in conjunction with the fill tube 7. When the said activating handle 13 is actuated, the activating handle 13 places upward vertical tension on the chain 14 which in turn raises the flapper 8 allowing water in the water tank 6 to exit the water tank 6 and enter the toilet bowl 9 to wash away the human waste. Simultaneously, the water level is lowering this activates the external pressurized water supply line to start flowing in the fill tube 7, flowing down the tube into the rim of the toilet bowl 9 flowing around the rim of the toilet bowl 9. Water exits the rim of the toilet bowl 9 through the rims openings 12. This water exiting from the rims openings 12 results in the rinsing/cleaning of the toilet bowl 9. During non-flushing periods, the fill tube 7, which is also in direct communication to the toilet bowl 9, maintains an open air passage from the water tank 6 to the toilet bowl 9. The device utilizes this passage from the toilet bowl 9 via the fill tube 7 and water tank 6 in order to pull the malodorous air up from the toilet bowl 9 through the file tube 7 and into an area within the water tank 6. The device is located internally of the water tank 6 being above the stored water level 2 and filters the malodorous odors, which are associated with human waste, from the air confined in the water tank 6. The malodorous odors are pushed through the housing 1 and after the malodors are removed, the filtered air is moved into an adjacent air space just above the housing 1. This prevents these malodorous odors from saturating the surrounding area of the toilet, individuals and clothing.

Figure 2:
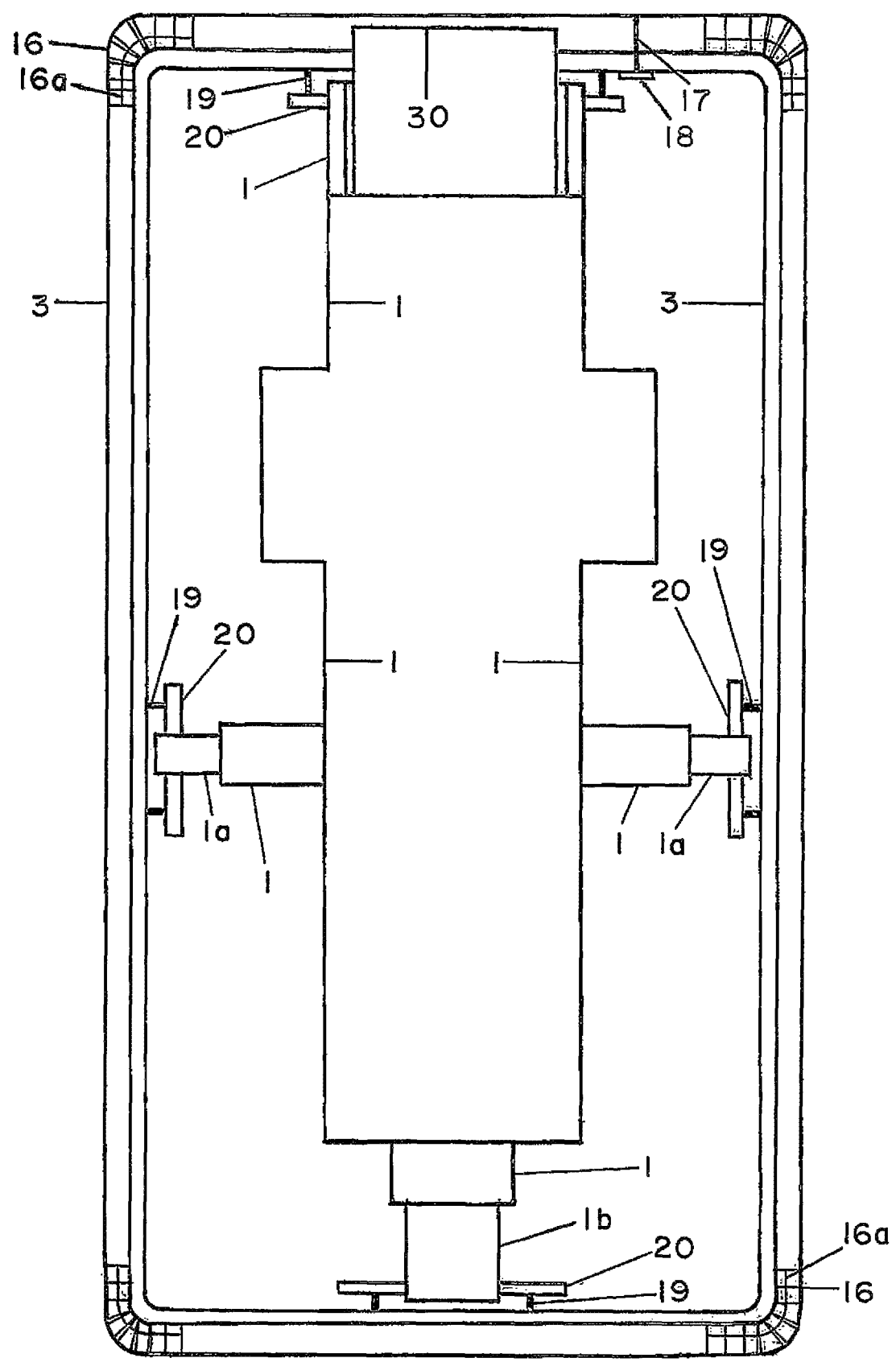
FIG. 2 is a top planar view of the water tank with the device's riser, support hooks, header and housing.

The components of the device are described in more detailed by the following figures. FIG. 2 is a plan view showing the layout of the riser 3 and a general device layout. Now referring to FIG. 4, the riser 3 consists of a thin caulking tape 34 where the thin caulking tape 34 is a fraction narrower than the water tank 6 wall thickness. The thin caulking tape 34 preferably has adhesive on the top and on the bottom and will be secured to the entire perimeter of the water tank 6 walls. The riser 3 is then placed on the caulking tape 34 with the horizontal member of the riser 3 adhered to the caulking tape 34 while simultaneously holding the lower portion of the vertical member of the riser 3 flush to the inside of the water tank 6 wall. The riser 3 as shown FIG. 4 also depicts other components which include a bracket support 19, a bracket support header 20 and a foam seal 31, which will be discussed later. Now referring to FIG. 2 and the four segmented corners 16 of the riser 3, the horizontal member of the riser 3 are cut perpendicular to the vertical member into small segments which are centered several inches on each side of calculated corner distances to allow the riser 3 to fit all toilets and their different radiuses, sizes, and shapes. This segmentation is sealed on top of a horizontal surface of the caulking tape 16a, each horizontal surface of the caulking tape 16a having a length to cover the segmented corners 16. The thin caulking tape 34 is a fraction less than the width of the water tank 6 wall width. This caulking tape 34 is to fill and all voids in the riser 3 made by the differences between the cut segments of the riser 3 and the tanks walls 6 perimeter ensure the water tank 6 remains a confined air space.

Now referring to FIGS. 2-5, there are four locations where the bracket supports 19 and the bracket support headers 20 combined are intended to be placed. Both of the bracket supports 19 and the bracket support headers 20 are made of thin, non-corrosive, lightweight durable material.

The two bracket supports 19 for holding the fixed support component under the exhaust tube 30 are centered equal distance each way from the center of the adjacent water tank wall. The bracket supports 19 are permanently attached to the side of the device at the vertical member of the riser 3. This permanent attachment is preferably done during the production of the riser 3. The length of the bracket support header 20 is longer than the corresponding bracket support 19 and is preferably the distance between corresponding bracket support 19 plus one quarter of an inch. This additional length will keep the bracket support header 20 from sliding along while giving additional space for the placement of a plurality of support bracket end caps 20a which are permanently secured to the bracket support headers 20.

Now referring to FIG. 2, the beginning point 17 of the riser 3 which is created by cutting the riser 3 during installation on site. Component flexible tape 18 is provided and is preferably a thin single sided adhesive. The component flexible tape 18 is placed on the inside covering this cold joint made on site in order to adhere to both segments of the riser 3 together and also to ensure the riser 3 remains airtight. The location of the tubular exhaust pipe 30 which is also referenced on FIG. 2.

Figure 4:
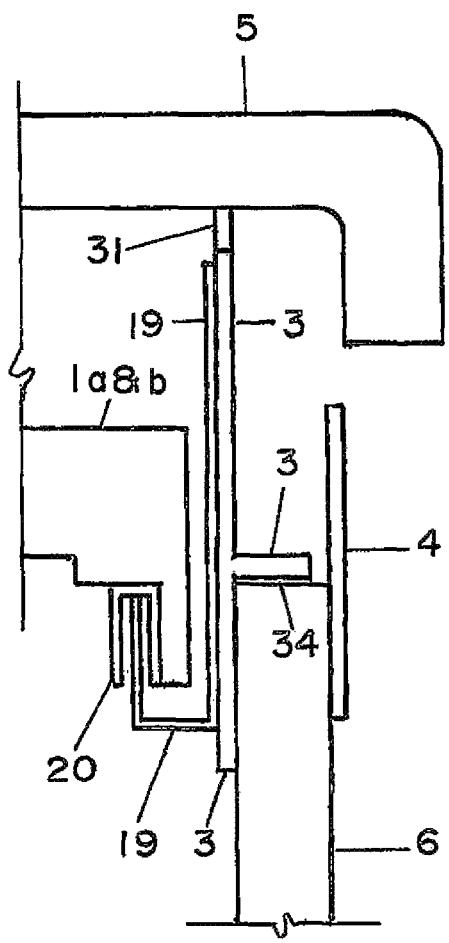
FIG. 4 is a detailed cross-sectional view partially showing a top section of the water tank depicting the water tank lid and water tank walls, the riser, bracket support, support bracket header and support arm.
Figure 3:
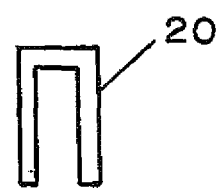
FIG. 3 is a cross-sectional view through the centerline of a support bracket header.
Figure 5:
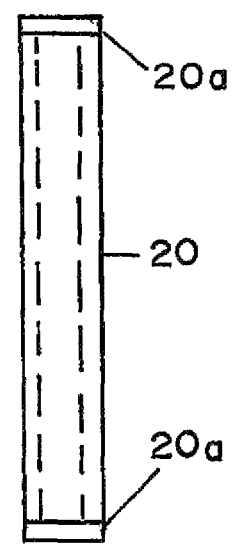
FIG. 5 is a plan view of the support bracket header with end caps shown.

Now referring to FIG. 3, a cross sectional view at the center of the previously mentioned bracket support header 20 is shown which is used to support the supporting arms of the device and are placed over two bracket supports 19. FIG. 4 is a cross sectional view in the riser 3 detailing the riser 3 and all adjacent components. A foam sealer 31 is used to maintain a space between the water level 2, the water tank lid 5 and inside the walls of the tank 6 airtight. The foam sealer 31 is permanently adhered to the riser 3. The bracket support 19 aid in the supporting of the water tank lid 5 and are permanently adhered to the riser 3. The bracket support 19 seats onto the support bracket header 20. Also observed on this FIG. 4 is a partial segment of the supporting arms 1a and 1b (collectively as 1 a & b).

Figure 6:
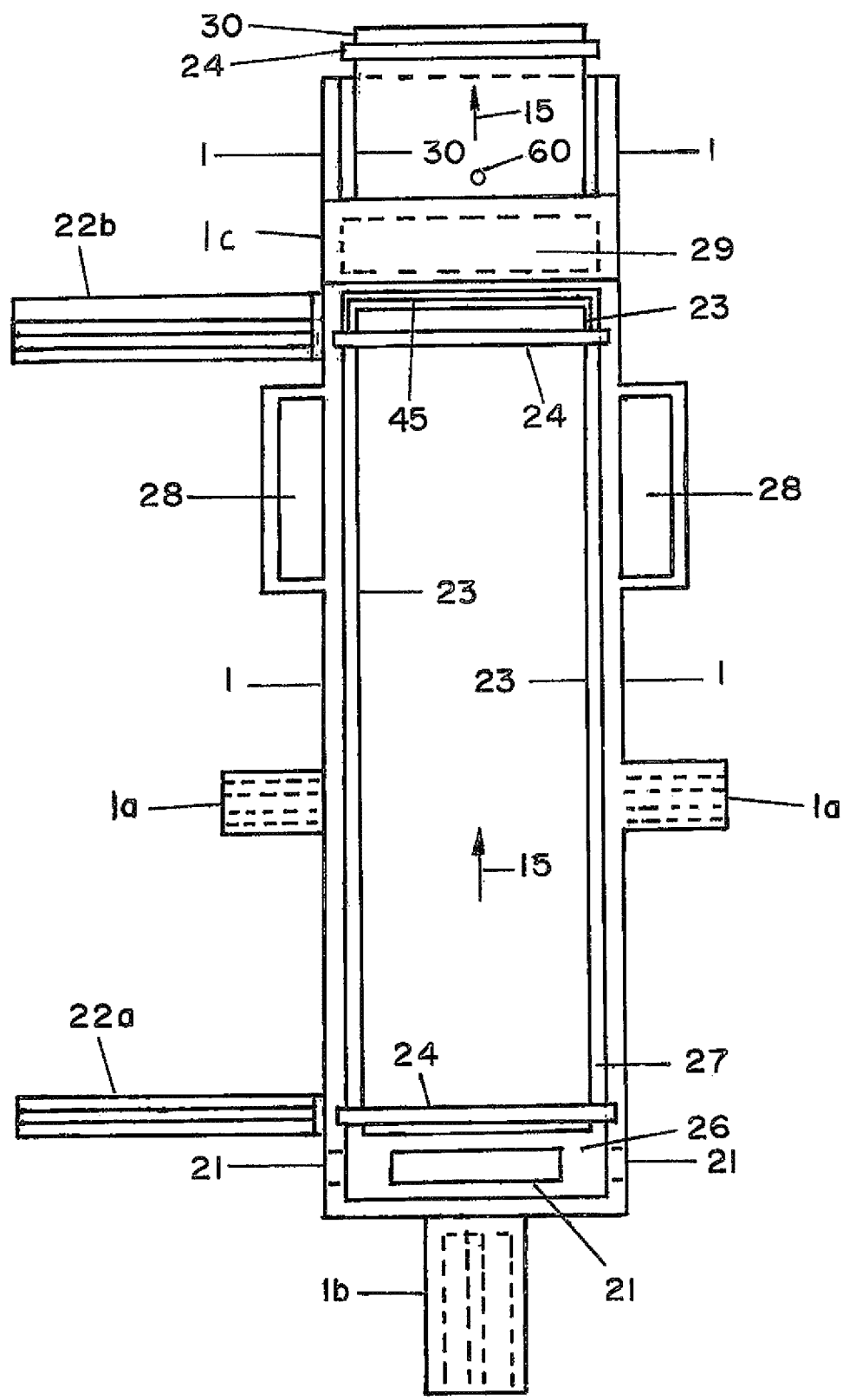
FIG. 6 is a planar view of a device housing, filler tube, exhaust tube, and chambers. Further illustrated is the air flow direction shown with arrows.

Now referring to FIG. 6, provided is of a plan view of the entire housing 1 of the device and numerous individual components and the individual chambers. These chambers are designated as an intake chamber 26, a filter chamber 27, a battery storage chamber 28, a micro fan chamber 29 and a tubular exhaust tube 30. A vacuum release 60 is installed on the tubular exhaust tube 30 to prevent a housing "air lock" which may happen during the flush cycle. After the installation of the riser 3, the seal should be airtight. The direction of airflow generated by this device may be determined by the reference number air flow 15 which displays the direction of air flow by a pointed arrow and is found throughout these drawings. The fixed supporting arm located at the outlet side of this device shall be attached to its corresponding bracket support header 20 concurrently inserting the exhaust tube 30 into an opening in the riser 3 as shown in FIG. 13, FIG. 14, and FIG. 15. Referring back to FIG. 6, pivoting on the bracket support header 20, the device is then lowered to secure the three remaining male adjustable supporting arms. Two of the support bracket arms 1a on the sides and one support bracket arm 1b on the opposite end of the tubular exhaust 30 should resided over their respective bracket support headers 20 and secured with the appropriate bracket support headers 20. With the three male components of the adjustable supporting arms 1a&b (see FIG. 4) having been previously inserted into the corresponding female component referenced by 1a (see FIG. 6 and FIG. 7) for the two components on the sides of the device referenced by 1b for the one component at the opposite end from the exhaust tube 30, where all three adjustable supporting arms are a part of the housing 1. These support bracket arms are now placed over and secured into their corresponding support bracket header 20 as shown in FIG. 4.

Now referring to FIG. 13, FIG. 14 and FIG. 15, the exhaust tube 30 is secured into the riser 3 with all the components in order to ensure the exhaust tube 30 is also airtight. The FIG. 13 illustrates the components needed to achieve this airtightness. It is preferred that all of these components are made of the same lightweight, durable, non-corrosive material used throughout this device, unless otherwise noted. These components are more particularly described as follows: the foam sealer 31, a tubular exhaust header 32, component flexible tape 18 and a centerline of screw hole 33. A screw should be used that is of a small diameter and should correspond with the screw hole. The screw is preferred to be stainless steal and securable by a Phillips head screw with adequate length to secure the tubular exhaust header 32 to a plurality of riser columns 3a. The riser columns 3a should reside flush with the edge of the hole in the riser 3. The omission of the riser 3 material at this location is for the insertion of the tubular exhaust pipe 30, thus becoming part of the riser 3 which ensures the air is confined inside the water tank 6. Securing of the tubular header 32 is accomplished by screwing the screws into the screw holes 33. This action secures the tubular exhaust header 32 by concurrently compressing a gasket 24, which is manufactured permanently around the entire perimeter of the tubular exhaust tube 30 (see figure FIG. 16 for details) ensures that the design is airtight. A thin piece of flexible tape 18 is adhered to all of the cold joint areas of the vertical member of the tubular exhaust header 32. This covering of all cold joints means the flexible tape 18 should lap the cold joint and adhere onto both sides of all the cold joints.

Figure 16:
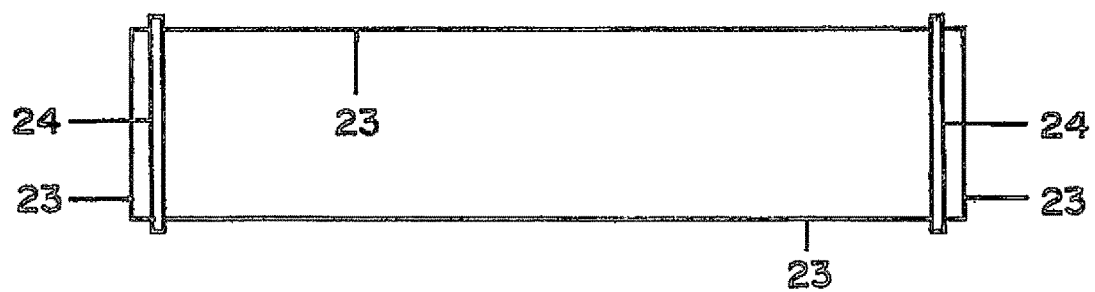
FIG. 16 is a side view of a filter tube.
Figure 17:
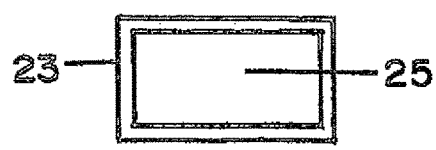
FIG. 17 is an end view of the filter tube.

Now referring FIG. 14, this drawing illustrates a cross sectional view of the inside of the tubular exhaust tube 30, including the bracket support 19 and corresponding bracket support header 20 as a reference. The foam sealer 31 assures that the air space in device area continues to be airtight. The tubular exhaust header 32 locks the tubular exhaust pipe 30 to a final position, compressing the gasket 24. Flexible tape 18 seals all the cold joints. The tubular exhaust tube 30 is an enclosed tube that allows the filtered air that is being pushed by the micro fans to exit from the confined space. The riser 3 seals the confined malodorous air in the desired space and the horizontal member of the riser 3 is a platform for the compression of the gaskets 24. Caulking tape 34 secures the riser to the water tank 6. The bracket support 19 provides a platform for the bracket support headers 20 to be placed on and concurrently strengthen the riser 3. The bracket support headers 20 give the supporting arms 1 a & b and the fixed arm a place to carry their respective loads and secure the device. Air flow 15 arrows depict the proposed air flow direction. The housing 1 is the main structure of the device. FIG. 15 is a plan view of the previous detailed areas drawn in FIG. 13 and FIG. 14. Referring to FIG. 16, this figure is a side view (the end view is identical for each end) of a tubular filter 23. FIG. 17 illustrates a mesh 25 which is permanently adhered to the tubular filter 23. The mesh 25 ensures confinement of the air filtering material inside of the tubular filter 23. Working in conjunction with the micro fans, malodorous air enters in one end of the tubular exhaust tube 30. The malodorous air travels the entire length of the tubular filter 23 which is being filtered by the filter material confined inside the tubular filter 23. The filter material is well known in the art. Carbon air filters are the most common filters used to remove malodor. The exiting air from the tubular filter 23 results in odorless air.

Figure 18:
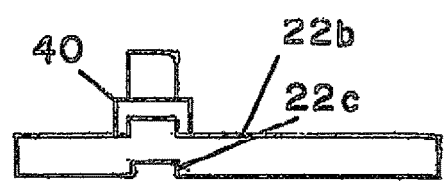
FIG. 18 is an end view of a securing and sealing component labeled 22*b* in FIG. 6 and FIG. 7.
Figure 19:
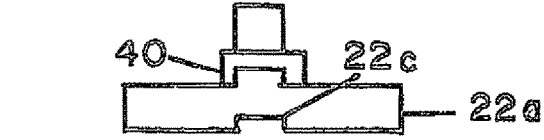
FIG. 19 is an end view of the securing and sealing component labeled 22*a* in FIG. 6.
Figure 20:
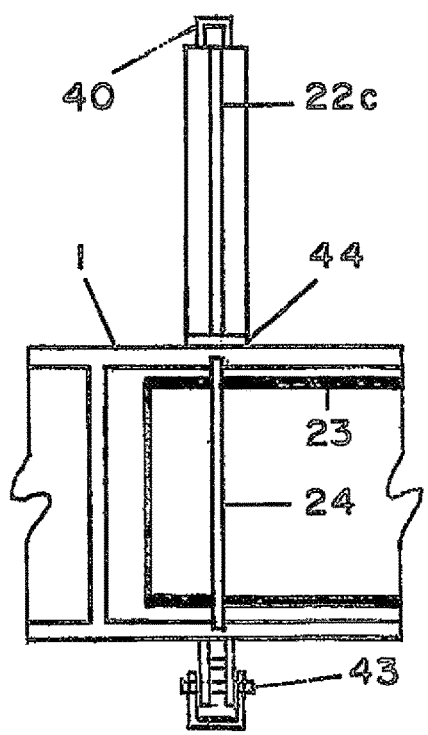
FIG. 20 is a plan view of the securing and sealing components as shown in FIG. 18 and FIG. 19.
Figure 21:
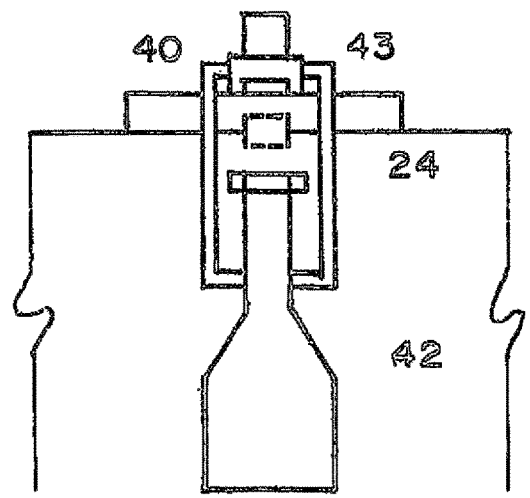
FIG. 21 is a side view of a locking component for the securing and sealing components labeled 22*a* and 22*b* in FIG. 6.

Now referring to FIG. 18, a larger swing arm 22b, a swing arm hook 40 and a gasket seeding grove 22c are shown. FIG. 19 is a drawing of the smaller swing arm 22a, a swing arm hook 40 and a gasket seeding grove 22c. FIG. 20 and FIG. 21 are drawings that are a general plan view of the securing and sealing device, which is mirrored at the opposite end of the tubular filter 23 except for the width of the larger swing arm 22b. FIG. 20 displays the following components: the device housing 1, the tubular filter 23, the gasket 24, the swing arm hook 40, a swing arm lock 43, and the gasket seeding grove 22c. The preferred gasket sealing device for 22a and 22b is similar to the locking device of fruit preservative jars. With this mechanism, the device operates as such: after the tubular filter 23 has been installed in its correct location within the device, the smaller swing arm 22a or the larger swing arm 22b is rotated in a radial direction to a closed position on top of the housing 1. The center of the radius is where the hinge 44 is located. This action in turn inserts the gasket 24, located around the tubular filter 23, into the seeding grove 22c, where the grove of the seeding grove 22c is the full length of the swing arm. At this point, the bail wire of the locking attachment is secured over the swing arm hook 40 which in turn moves to swing the swing arm handle 42 to an upwards position. Then with a downward motion of the swing arm handle 42, the locking mechanism turns and places the tubular filter 23 in its sealed and functioning position. This action also keeps the malodorous air in its confined space prior to the filtering process.

Figure 22:
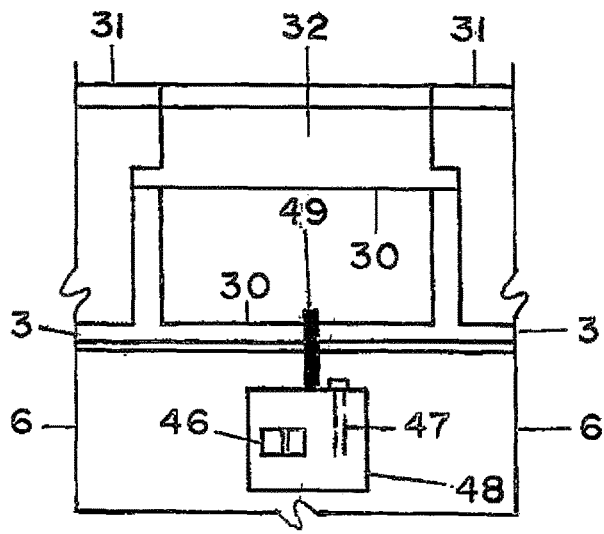
FIG. 22 is a side view of an on/off switch and a charging port panel along with a suggested location for the operation of the device which could be located at an end part of the exhaust.
Figure 23:
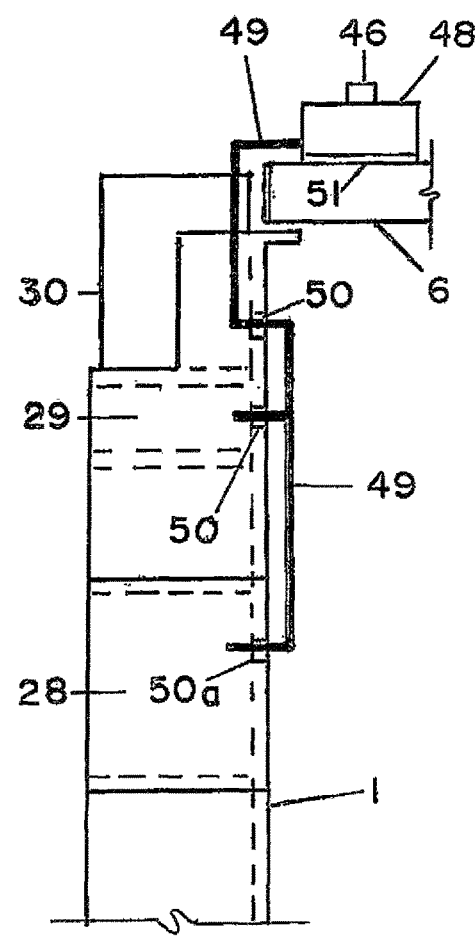
FIG. 23 is a top plan view of a suggested wiring diagram for the device.
Figure 24:
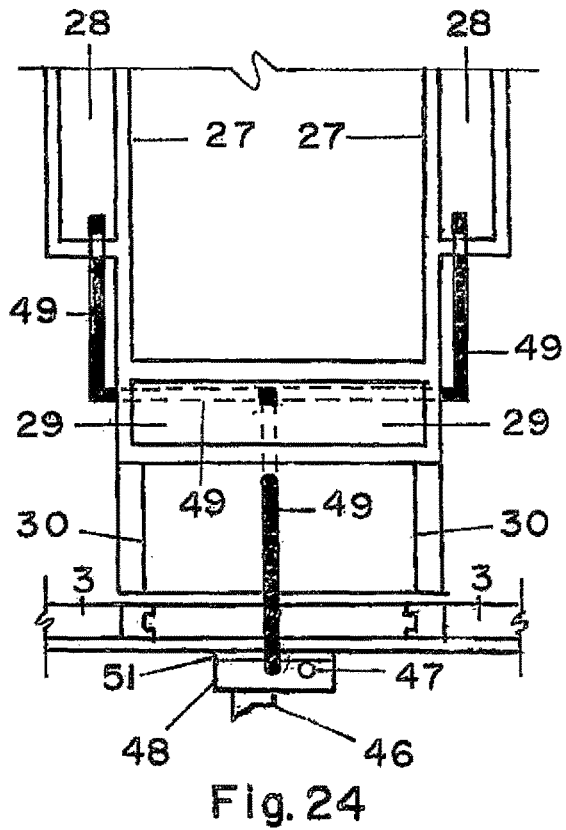
FIG. 24 as a side view of the suggested wiring diagram for the device.

Now referring to FIG. 22, FIG. 23, and FIG. 24, the preferred electrical wiring schematic is provided and includes all of the associated components which are being referenced with the following numbers: an on/off switch 46, a charging port 47, a panel 48, a set of electrical wires 49, a sealed access hole 50, an unsealed access hole 50a and a double sided adhesive strip 51. It is preferred that all of these electrical components should be installed during the manufacturing process. The materials used are determined by the manufacturer. It is preferred that the set of electrical wires 49 follow this suggested route: the panel 48 is located on the same end as the tubular exhaust tube 30 and the electrical wire 49 is placed internally in the cavity of the tubular exhaust pipe 30. The electrical wire 49 is installed to a point close where the tubular exhaust pipe 30 is sealed and joined to the housing 1 during manufacturing. The electrical wire 49 is then turned downward towards the existing the tubular exhaust tube 30 and passes through the bottom of the tubular exhaust pipe 30 passing through the sealed hole 50. This sealed hole 50 has been sealed during manufacturing after the electrical wires 49 have been installed. The electrical wire 49 continues passing through a sealed hole 50 in the housing 1. The electrical wires 49 are preferably located at the underside of this device. The electrical wires 49 may be attached to the bottom of housing 1 and continue until the wires splice to feed the micro fan chamber 29. The splice travels upwards and enters through a sealed hole 50. This sealed hole 50 has been sealed during manufacturing, to become the power supply in the micro fan chamber 29. The splice then continues in both directions after splitting in order to feed one or more battery chambers 28, entering through an unsealed access hole 50a in the bottom of the housing 1, which is also the bottom of the two battery chambers 28.

Figure 7:
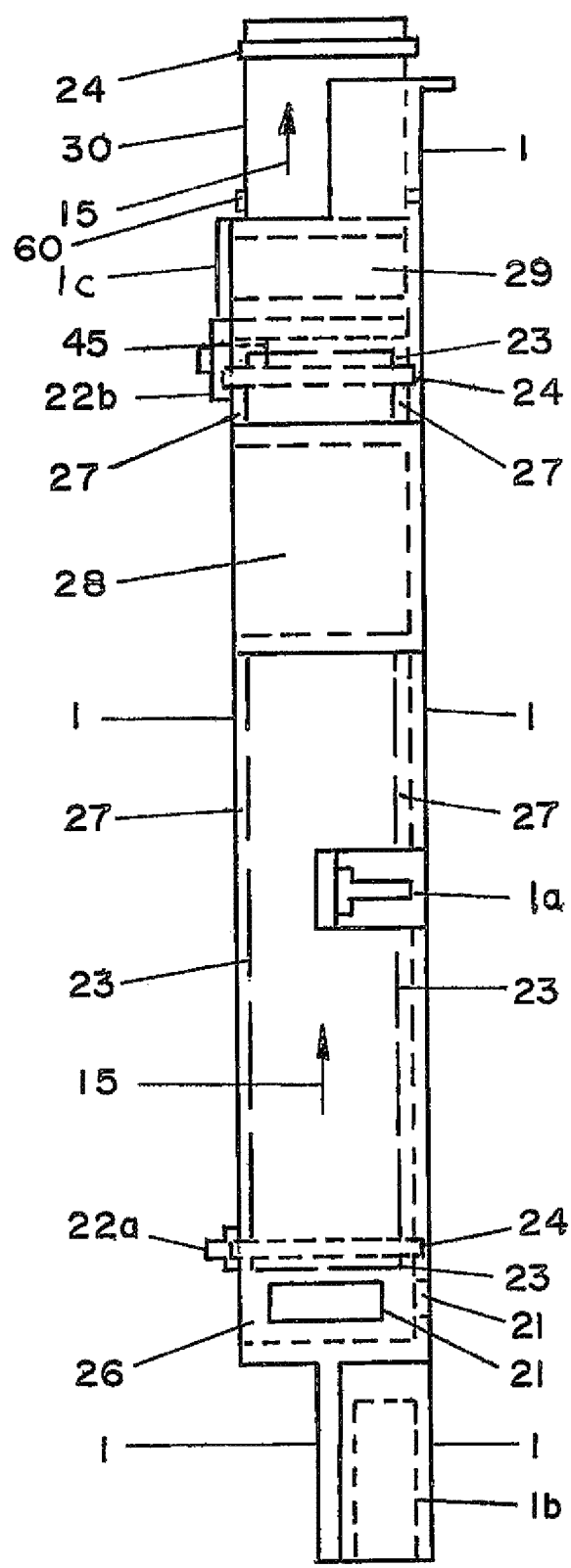
FIG. 7 is a side view of the device housing with the individual chambers shown. Further illustrated is the air flow direction shown with arrows.
Figure 8:
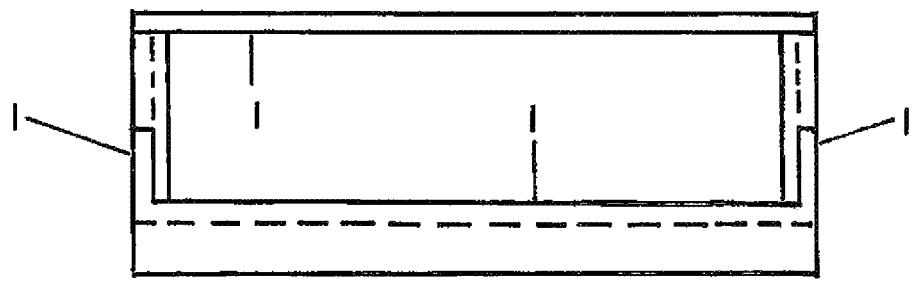
FIG. 8 is an end view of a fixed supporting bracket which is a part of the device housing located where the exhaust tube resides.
Figure 9:
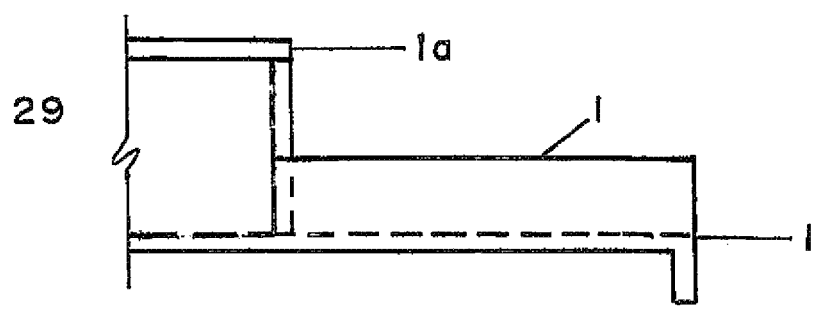
FIG. 9 is a side view of the fixed supporting bracket.
Figure 10:
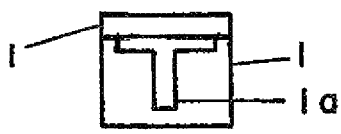
FIG. 10 is an end view of a female component of an adjustable supporting bracket. Two adjustable supporting brackets are provided and located on both sides of the housing. The female components will receive a corresponding male component of an adjustable supporting bracket labeled 1 *a* & *b* in FIG. 12.
Figure 11:
FIG. 11 is an end view of the female component of the adjustable supporting bracket located on the opposite end of the housing exhaust tube that will receive the male component of the adjustable supporting bracket labeled 1 *a* & *b* in FIG. 12.
Figure 12:
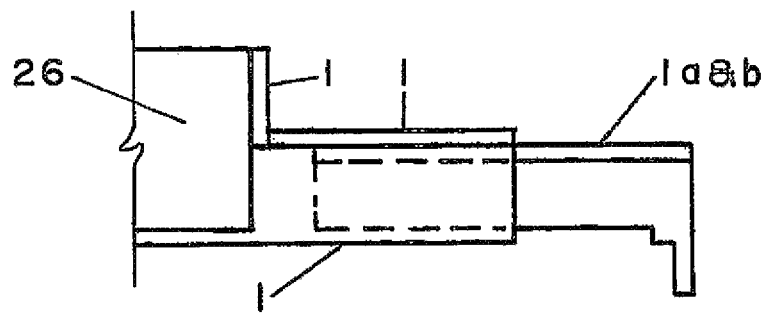
FIG. 12 is a side view of one of the three adjustable supporting brackets previously mentioned in FIG. 10 and FIG. 11. The male component labeled 1 *a* & *b* is inserted into the female components to complete the support of the device housing. The male component slides in and out of the fixed female component to meet the dimensions of the toilet water tank.

FIG. 6 and FIG. 7 are a plan view of the main device where broken lines are shown to denote hidden chambers in order to allow for easier reference of the chambers. Some of the references in the figures are identified as a filter chamber gasket 45 and a micro fan cap 1c. The micro fan cap 1 c may be applied to the housing 1. It is preferred that the manufacturer determine when the micro fan cap 1c should be secured to the housing 1 due to the installation of the micro fans in the micro fan chamber 29. After installation has been completed of the device and the device is ready to be "turned on," the air movement 15 is activated. Upon switching the on/off switch 46 located on the exterior of the water tank 6, direct communication is initialized between a power source. The power source is preferred to be batteries in the battery storage chambers 28. The micro fans are preferably located in the micro fan chamber 29. This initialization of the micro fans produces a negative pressure on everything upstream of the micro fans and a positive pressure downstream of the micro fans. This pressure forces the confined air in the water tank 6 to be pulled into the intake chamber of this device gaining access through a plurality of air holes 21 in the intake chamber 26. Accompanying the plurality of air holes 21 is the housing 1 unenclosed top over the air intake chamber 26. The malodorous air is then pulled into the tubular filter 23. The tubular filter 23 has a gasket 24 which is compressed by the action of locking the smaller swing arm 22a with its corresponding swing arm lock 43, thus ensuring the confined malodorous air is pulled directly into the tubular filter 23 through the mesh 25, confining the air therein. The continued pulling moves the malodorous air through the entire length of the tubular filter 23. The filter material within the tubular filter 23 removes the malodorous smells and exits the opposite end of the tubular filter 23. The filtered air then moves to an outlet end of the tubular filter 23 and is in confined in a sealed area. This sealed area has been sealed to avoid the filtered air being mixed with any outside malodorous air confined inside the water tank 6. This sealing is accomplished by locking the larger swing arm 22b which also compresses the gasket 24 and compresses the filter chamber gasket 45. The filter chamber gasket 45 is a gasket located near the top of the outlet end of the tubular filter 23 on the three unsealed walls of the housing 1 to ensure no malodorous enters this closed system. The filtered air is then pulled from the sealed downstream end of the filter tube 23 and into the micro fan chamber 29. The air then moves across the micro fans and is pushed in a positive manner. The pushed air leaves the micro fan chamber 29 and enters into the tubular exhaust tube 30. The tubular exhaust tube 30 is preferably adhered to the housing 1, and more preferably adhered previously during manufacturing. The pushed air then exits the tubular exhaust tube 30 through an open end of the tubular exhaust tube 30 (see FIG. 14) which terminates beyond the riser 3.

While a particular embodiment of the toilet odor elimination device has been described herein, it will be appreciated by those skilled in the art that changes and modifications may be made thereto without departing from the invention in its broader aspects and as set forth herein.

What is claimed:

1. A toilet odor elimination device that resides below a water tank lid of a water tank comprising:
    a housing with a plurality of supporting arms, wherein said housing houses an intake chamber, a filter chamber in operational relationship to a micro fan chamber, a tubular exhaust tube and an at least one battery storage chamber;
    a plurality of bracket supports in a structural relationship to said plurality of supporting arms to support said housing in a suspended manner;
    a riser fixedly attached to said plurality of bracket supports and wherein said riser raises the level of the water tank lid to a position higher than the water tank lid; and
    an on/off switch in electrical relationship to a power source located in said at least one battery storage chamber, wherein said on/off switch actuates a plurality of micro fans located in said micro fan chamber.

2. The toilet odor elimination device of claim 1, wherein said filter chamber comprises of a tubular filter made of filter material, wherein the filter material removes malodor from malodor air to create filtered air.

3. The toilet odor elimination device of claim 2, wherein a mesh is permanently adhered to said tubular filter.

4. The toilet odor elimination device of claim 3, wherein the tubular filter is secured by a gasket that compresses when a swing arm lock is engaged by a swing arm handle.

5. The toilet odor elimination device of claim 2, wherein the filtered air exits through a tubular exhaust tube located on an opposite side of the tubular filter.

6. The toilet odor elimination device of claim 2, wherein a plurality of air holes is located on said housing around said air intake chamber.

7. The toilet odor elimination device of claim 1, wherein said plurality of supporting arms are extendable.

8. The toilet odor elimination device of claim 1, wherein said riser is secured to the water tank lid by a foam sealer.

9. The toilet odor elimination device of claim 1, wherein said riser is fixedly secured to a wall of the water tank with a horizontal member of the riser.

10. The toilet odor elimination device of claim 9, wherein a lower portion of a vertical member of the riser resides flush to an inside part said wall of the water tank.

11. The toilet odor elimination device of claim 9, wherein a micro fan cap is secured to said housing.

12. A toilet odor elimination device that resides below a water tank lid of a water tank turning malodorous air into filtered air, the toilet odor elimination device comprising:
    a housing with a plurality of supporting arms, wherein said housing houses an intake chamber, a filter chamber comprises a tubular filter designed to remove malodor with a carbon filter and is in operational relationship to a micro fan chamber, a tubular exhaust tube and an at least one battery storage chamber;
    a plurality of bracket supports in a structural relationship to said plurality of supporting arms to support said housing in a suspended manner;
    a riser fixedly attached to said plurality of bracket supports and wherein said riser raises the level of the water tank lid to a position higher than the water tank lid and said riser is fixedly attached to the water tank lid;
    wherein said tubular exhaust tube pushes the filtered air out said riser; and
    an on/off switch in electrical relationship to a power source located in said at least one battery storage chamber.

* * * * *